US009526491B2

(12) United States Patent  
McClellan

(10) Patent No.: US 9,526,491 B2  
(45) Date of Patent: Dec. 27, 2016

(54) DERMAL TABS

(71) Applicant: William T. McClellan, Morgantown, WV (US)

(72) Inventor: William T. McClellan, Morgantown, WV (US)

( * ) Notice: Subject to any disclaimer, the term of this patent is extended or adjusted under 35 U.S.C. 154(b) by 333 days.

(21) Appl. No.: 14/200,356

(22) Filed: Mar. 7, 2014

(65) Prior Publication Data

US 2014/0257386 A1 Sep. 11, 2014

Related U.S. Application Data

(60) Provisional application No. 61/774,864, filed on Mar. 8, 2013.

(51) Int. Cl.
| | | |
|---|---|---|
| *A61B 17/04* | (2006.01) | |
| *A61F 2/10* | (2006.01) | |
| *A61B 17/00* | (2006.01) | |

(52) U.S. Cl.
CPC ........... *A61B 17/0401* (2013.01); *A61F 2/105* (2013.01); *A61B 90/02* (2016.02); *A61B 2017/00526* (2013.01); *A61B 2017/00747* (2013.01); *A61B 2017/00969* (2013.01); *A61B 2017/0464* (2013.01); *A61F 2220/0008* (2013.01); *Y10T 29/49* (2015.01)

(58) Field of Classification Search
CPC ................. A61B 17/0401; A61B 2017/00969; A61B 2017/0464; A61F 2/0063; A61F 2/077; A61F 2/105; A61F 2/12; A61F 2002/081; A61F 2220/0008
See application file for complete search history.

(56) References Cited

U.S. PATENT DOCUMENTS

| | | | |
|---|---|---|---|
| 4,060,081 A | 11/1977 | Yannas et al. | |
| 4,796,036 A | 1/1989 | Misono et al. | |
| 7,641,958 B2 | 1/2010 | Berman et al. | |
| 7,985,263 B2 | 7/2011 | Berman et al. | |
| 2005/0021141 A1 | 1/2005 | Bleyer et al. | |
| 2009/0125107 A1* | 5/2009 | Maxwell .................... | A61F 2/12 623/8 |
| 2010/0023029 A1* | 1/2010 | Young ................... | A61F 2/0063 606/151 |
| 2010/0217388 A1 | 8/2010 | Cohen et al. | |
| 2011/0015760 A1* | 1/2011 | Kullas ................... | A61F 2/0063 623/23.72 |

* cited by examiner

*Primary Examiner* — Ryan J Severson  
*Assistant Examiner* — Christian Knauss  
(74) *Attorney, Agent, or Firm* — Andrew D. Wright; Roberts Mlotkowski Safran Cole & Calderon, P.C.

(57) ABSTRACT

Approaches for implanting a donor dermis (e.g., skin) in or on a patient body are provided. A device includes a piece of donor dermis and at least one tab formed in or on the donor dermis, wherein the tab is adapted for accepting a suture. A method includes manufacturing a device including a piece of donor dermis and at least one tab formed in or on the donor dermis, wherein the tab is adapted for accepting a suture. Another method includes fastening tissue using a device including a piece of donor dermis and at least one tab formed in or on the donor dermis, wherein the tab is adapted for accepting a suture.

18 Claims, 2 Drawing Sheets

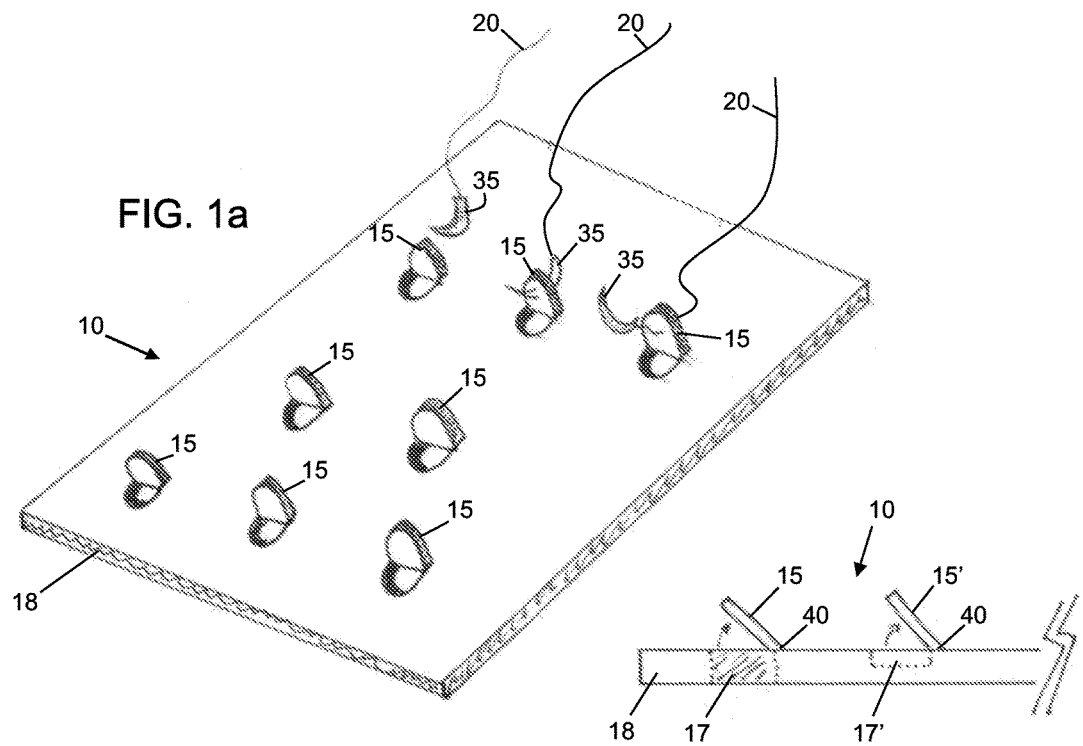
FIG. 1a
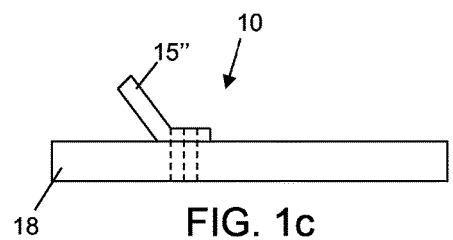
FIG. 1b
FIG. 1c

DERMAL TABS

CROSS REFERENCE

This application claims domestic priority to U.S. Provisional Patent Application No. 61/774,864, filed Mar. 8, 2013, the contents of which are incorporated by reference in their entirety.

FIELD OF THE INVENTION

The invention generally relates to medical devices and associated methods of manufacture and use, and more particularly to donor dermis (e.g., skin) that is implanted in or on a patient body.

SUMMARY

In a first aspect of the invention, there is a device comprising: a piece of donor dermis; and at least one tab formed in or on the donor dermis, wherein the tab is adapted for accepting a suture. In embodiments, the at least one tab is a full thickness portion of the donor dermis. In other embodiments, the at least one tab is a partial thickness section of the donor dermis. In embodiments, the at least one tab has one end still connected to the donor dermis and can be pivoted to extend away from the donor dermis. In embodiments, the at least one tab is another section of donor dermis that is connected to the first section of donor dermis, e.g., by adhesive, suture, rivet, staple, etc. In embodiments, the at least one tab comprises a plurality of tabs. The plurality of tabs may be arranged in a predefined pattern on the donor dermis. The predefined pattern may correspond to location of a tissue of a patient body to which the donor dermis is to be attached.

In another aspect of the invention, there is a method of manufacturing a device comprising: a piece of donor dermis; and at least one tab formed in or on the donor dermis, wherein the tab is adapted for accepting a suture. In embodiments, the method comprises forming the tabs in the piece of donor dermis.

In another aspect of the invention, there is a method of fastening tissue using a device comprising: a piece of donor dermis; and at least one tab formed in or on the donor dermis, wherein the tab is adapted for accepting a suture. In embodiments, the method comprises suturing the at least one tab to subcutaneous tissue of a patient. In embodiments, the method comprises: suturing a first end of the donor dermis to a pectoral muscle of the patient; and suturing a second end of the donor dermis to a chest wall of the patient.

In another aspect of the invention, there is an implant device comprising a donor dermis with at least one tab as described herein. In additional aspects of the invention, there is a method of fastening tissue using a donor dermis with at least one tab as described herein.

BRIEF DESCRIPTION OF THE SEVERAL VIEWS OF THE DRAWINGS

The present invention is described in the detailed description which follows, in reference to the noted plurality of drawings by way of non-limiting examples of exemplary embodiments of the present invention.

FIGS. 1a, 1b, and 1c show aspects of a donor dermis with dermal tabs in accordance with aspects of the invention.

DETAILED DESCRIPTION

Figure 2:
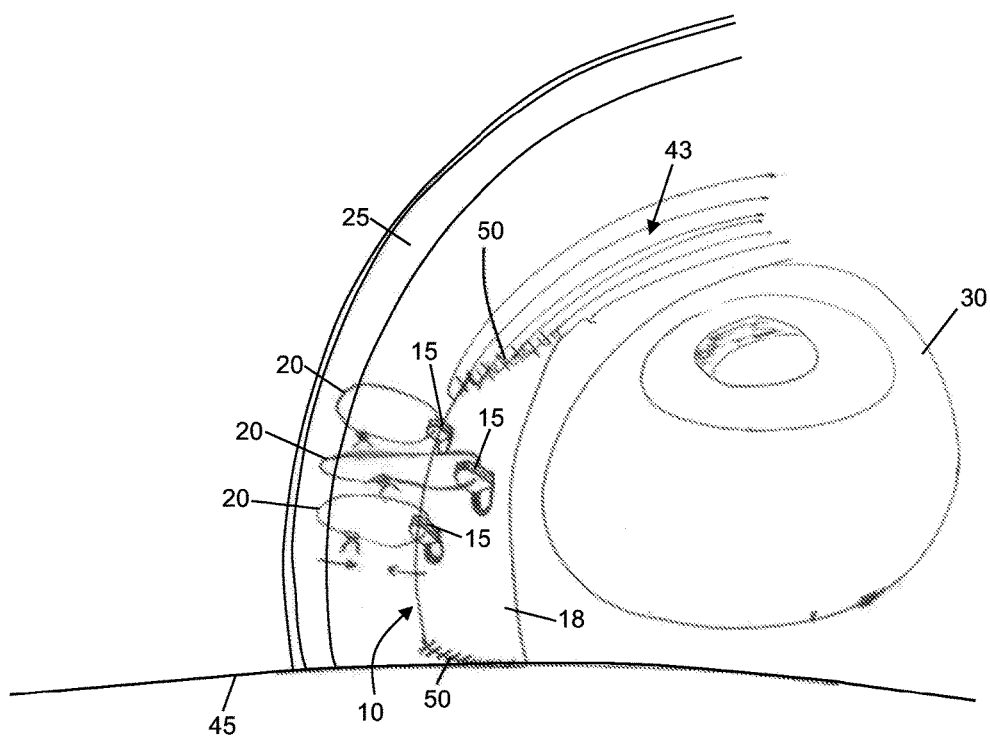
FIG. 2 shows an exemplary implant of a donor dermis with dermal tabs in accordance with aspects of the invention.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

In accordance with aspects of the invention, FIGS. 1a and 1b show a portion of donor dermis 10 that is modified by creating at least one tab 15 in the donor dermis 10 from a section of the donor dermis 10 (also referred to as donor allograft, donor allograft dermis, and allograft dermis). The tab 15 may be mechanically created by cutting a full or partial thickness section of the donor dermis 10 to create a hinged flap of the donor dermis 10. Embodiments thus include creating a tab 15 (full or partial thickness) on the existing allograft dermis 10 mechanically. As shown in FIG. 1b, the tab 15 may be a full thickness cut of the donor dermis 10, in which case a hole 17 is created entirely through the thickness of the main layer 18 of the donor dermis 10. As also shown in FIG. 1b, the tab 15' may be a partial thickness cut of the donor dermis 10, in which case a hole 17' is created through less than the entire thickness of the main layer 18 of the donor dermis 10. The tab 15 can stick up or be flush that comes up with a little teasing. Alternatively, the tab 15 can be a thicker area of dermis that is cut in relief by removing surrounding tissue to create a small mound of dermis to grab. Alternatively, a separate small piece of dermal tissue can be adhered (sewn, glued, fixed) to the allograft dermis 10 to create the tab 15", as depicted in FIG. 1c. The tabs 15 can be a multitude of sizes and or shapes or numbers of them on the donor allograft 10.

FIG. 2 shows an exemplary implant of a donor dermis 10 with dermal tabs 15 in accordance with aspects of the invention. An advantage of the donor dermis 10 with dermal tabs 15 is the ability to safely place a suture 20 between the dermal tab 15 and a subcutaneous skin layer 25. Stitching sutures 20 through the tabs 15 instead of through the main layer 18 of the donor dermis 10 advantageously decreases the chance of accidentally puncturing something (such as a tissue expander 30 that is behind the donor dermis 10 in the patient body) during the stitching. By placing a "quilting" stitch 20 between these two layers 18 and 25, the chance of fluid/blood build up between the two layers 18 and 25 is lessened because the two layers are forced to become intimate by the stitch. Additionally, the allograft dermis 10 will be ingrown by the host tissue from the host dermis (e.g., layer 25) which it is touching. For the host (e.g., layer 25) to grow into the allograft dermis 10, it is advantageous for it to be in intimate contact and not experience shear forces or other movement between the layers 18 and 25. The dermal tab 15 serves as a mechanical joining by suture of these two layers 18 and 25.

By having the tab 15 it becomes much easier the grab the allograft dermis 10 with a needle without fear of poking something behind the allograft dermis 10, such as a tissue expander 30 in the breast or bowel when fixing a hernia.

Also, suturing the allograft dermis 10 to the subcutaneous skin (e.g., layer 25) may quicken the in-growth of the host into the donor dermis 10 because of the stability from shear and potential of fluid separation of the layers. This would be very helpful for patients.

In embodiments, and as shown in FIGS. 1a, 1b, and 2, the dermal tabs 15 are formed in the donor dermis 10 by cutting, punching out, etc. Each tab 15 is left attached to the donor dermis 10 during the tab-forming process, e.g., one end of the tab 15 is uncut at the donor dermis 10, e.g., as shown at location 40. The tabs 15 can be moved relative to the donor dermis 10, e.g., pivoted to extend outward from the donor dermis 10 with the one end of the tab 15 still attached to the donor dermis 10. The tab 15 can be used as a portion of the donor dermis 10 to pass a needle 35 and suture 20 through for the purpose of suturing the donor dermis 10 to a part of a patient body, e.g., the patient subcutaneous tissue 25, e.g., in the breast skin/dermis of the patient when implanting a tissue expander 30 in the patient. Ends of the donor dermis 10 may be sutured to the pectoral muscle 43 and/or the chest wall 45 without using tabs 15, e.g., as shown at sutures 50.

The donor dermis 10 may initially be a section of skin that is removed from (e.g., cut from) an organ or tissue donor, as is understood by those of skill in the art. A plurality of tabs 15 may be formed in a single section of donor dermis 10. The plural tabs 15 may be formed in a predefined pattern in the donor dermis 10 to optimize the locations for attachment to the patient, e.g., to optimize the locations at which the donor dermis 10 is sutured to the subcutaneous tissue. In addition to a predetermined pattern, the tabs 15 may be formed in any suitable size and shape, and any desired number of tabs may be used.

Embodiments of the invention include a donor dermis having one or more tabs as described herein. Further embodiments of the invention include a method of manufacturing a donor dermis having one or more tabs as described herein. Even further embodiments of the invention include a method of implanting in a patient a donor dermis having one or more tabs as described herein.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. A device, comprising:
a piece of donor dermis;
at least one tab formed in or on the donor dermis; and
a suture passing through the at least one tab, wherein the suture secures the at least one tab, and the donor dermis, to a tissue.

2. The device of claim 1, wherein the at least one tab is a full thickness portion of the donor dermis.

3. The device of claim 1, wherein the at least one tab has one end still connected to the donor dermis and can be pivoted to extend away from the donor dermis.

4. The device of claim 1, wherein the at least one tab comprises a plurality of tabs.

5. The device of claim 4, wherein the plurality of tabs are arranged in a predefined pattern on the donor dermis.

6. The device of claim 5, wherein the predefined pattern corresponds to a location of a tissue of a patient body to which the donor dermis is to be attached.

7. A device, comprising:
a piece of donor dermis; and
at least one tab formed in or on the donor dermis, wherein the tab is adapted for accepting a suture,
wherein the at least one tab is a partial thickness section of the donor dermis.

8. A method of manufacturing the device of claim 7, wherein the method comprises forming the at least one tab in the piece of donor dermis.

9. A method of fastening tissue using the device of claim 7, wherein the method comprises suturing the at least one tab to subcutaneous tissue of a patient.

10. The method of claim 9, wherein the method comprises:
suturing a first end of the donor dermis to a pectoral muscle of the patient; and
suturing a second end of the donor dermis to a chest wall of the patient.

11. The method of claim 10, wherein:
the suturing the first end of the donor dermis to the pectoral muscle comprises passing a suture through the first end of the donor dermis that is devoid of the at least one tab; and
the suturing the second end of the donor dermis to the chest wall comprises passing a first suture through the second end of the donor dermis that is devoid of the at least one tab.

12. The method of claim 11, wherein the suturing the at least one tab to subcutaneous tissue of a patient comprises passing a suture through the at least one tab and the subcutaneous tissue.

13. The method of claim 9, wherein the suturing the at least one tab to subcutaneous tissue of a patient comprises passing a suture through the at least one tab and the subcutaneous tissue.

14. A device, comprising:
a piece of donor dermis: and
at least one tab formed in or on the donor dermis, wherein the tab is adapted for accepting a suture,
wherein the at least one tab is another section of donor dermis that is connected to the piece of donor dermis.

15. The device of claim 14, wherein the at least one tab is another section of donor dermis that is connected to the piece of donor dermis by adhesive.

16. The device of claim 14, wherein the at least one tab is another section of donor dermis that is connected to the piece of donor dermis by suture.

17. The device of claim 14, wherein the at least one tab is another section of donor dermis that is connected to the piece of donor dermis by rivet.

18. The device of claim 14, wherein the at least one tab is another section of donor dermis that is connected to the piece of donor dermis by staple.

* * * * *